United States Patent [19]

Armstrong

[11] 4,126,680

[45] * Nov. 21, 1978

[54] TETRACYCLINE ANTIBIOTIC COMPOSITIONS

[75] Inventor: William W. Armstrong, Mill Neck, N.Y.

[73] Assignee: Pfizer Inc., New York, N.Y.

[*] Notice: The portion of the term of this patent subsequent to Apr. 19, 1994, has been disclaimed.

[21] Appl. No.: 791,627

[22] Filed: Apr. 27, 1977

[51] Int. Cl.$^2$ ..................... A61K 31/79; A61K 31/65
[52] U.S. Cl. ....................................... 424/80; 424/227
[58] Field of Search ................................. 424/227, 80

[56] References Cited

U.S. PATENT DOCUMENTS 4,018,889  4/1977  Armstrong ........................... 424/227

OTHER PUBLICATIONS

Chemical Abstracts, 57:15748(s) (1962).

Primary Examiner—Jerome D. Goldberg
Attorney, Agent, or Firm—Francis X. Murphy; Charles J. Knuth; Allen J. Spiegel

[57] ABSTRACT

Aqueous solutions of oxytetracycline, doxycycline or chlortetracycline in caprolactam or 2-piperidone are disclosed.

24 Claims, No Drawings

TETRACYCLINE ANTIBIOTIC COMPOSITIONS

BACKGROUND OF THE INVENTION

This invention relates to antibiotic compositions suitable for pharmaceutical use. More particularly, it relates to aqueous solutions of tetracycline antibiotics in caprolactam or 2-piperidone.

U.S. Pat. No. 3,957,980 discloses aqueous injectable solutions of doxycycline comprising a solution in water of from about 1% to 10% by weight of doxycycline, together with about 3 to 8 molar proportions of a phosphate salt selected from phosphoric acid, sodium or potassium orthophosphate, metaphosphate, pyrophosphate, tripolyphosphate or hexametaphosphate, and about 3 to 8 molar proportions of a pharmaceutically acceptable magnesium salt solution in said aqueous pharmaceutical composition, said composition having a pH value in the range of from about 1 to 3.5.

U.S. Pat. No. 3,674,859 discloses aqueous solutions of doxycycline containing from about 1% to 15% doxycycline and from about 5 percent to 40 percent by weight of polyvinylpyrrolidone having an average molecular weight that is in the range of from about 10,000 to about 60,000, said composition having a pH value in the range of from about 5 to about 8.

U.S. Pat. No. 2,980,584 discloses aqueous parenteral solutions of oxytetracycline metal complexes containing 25–80% of an acetic or lactic acid carboxamide, such as N,N-dimethylacetamide and N-($\beta$-hydroxyethyl) lactamide at a pH of 8.5–9.5. Concentrations of 10 to 100 mg./ml. are disclosed.

U.S. Pat. No. 2,990,331 discloses parenteral solutions of oxytetracycline hydrochloride and tetracycline hydrochloride containing about 50 mg./ml. having a pH value between 5 and 7, containing magnesium ions, an alkali bisulfite and a carboxylic acid amide, such as lactic acid-hydroxyethyl amide.

U.S. Pat. No. 3,062,717 discloses aqueous parenteral solutions of tetracycline calcium complexes containing 35–80% of an amide of acetic or lactic acid, such as N,N-dimethylacetamide or N-($\beta$-hydroxylethyl) lactamide, at a pH of 7 to 9.5. Concentrations of 10 to 100 mg./ml. are disclosed.

U.S. Pat. No. 3,557,280 discloses aqueous solutions of oxytetracycline containing 1 to 20% oxytetracycline, a magnesium compound and polyvinylpyrrolidone, 7.5 to 25%, at a pH of 8.0 to 9.5.

Belgian Pat. No. 825,656 discloses aqueous solutions of oxytetracycline containing 4 to 11% oxytetracycline, 20 to 30% of a polyethylene glycol, such as polyethylene glycol 400, a magnesium compound and 0.10 to 0.35% of a buffer, such as tris-(hydroxymethyl)-aminomethane at a pH of 8 to 9.

French Patent Publication No. 2,258,187 discloses aqueous solutions of oxytetracycline containing 50 mg./ml. of oxytetracycline, 5 to 7.49% polyvinylpyrrolidone and up to 24.9% of an acid amide containing one to six carbon atoms, such as dimethylacetamide, at a pH of 8 to 9.5.

U.S. Pat. No. 4,018,889 discloses oxytetracycline solutions containing from about 1 to 40 percent oxytetracycline in an aqueous vehicle containing from about 10 to 50 percent by weight of 2-pyrrolidone, about 0.8 to 1.3 molar proportions of a pharmaceutically acceptable magnesium compound soluble in the said solution, said solution having a pH value in the range of from about 7.5 to 9.5.

SUMMARY OF THE INVENTION

In accordance with this invention there is disclosed a liquid composition comprising an aqueous solution of a tetracycline antibiotic in caprolactam or 2-piperidone, said tetracycline being selected from the group consisting of oxytetracycline, doxycycline, chlortetracycline, and the pharmaceutically acceptable acid addition salts thereof.

This invention also discloses a preferred oxytetracycline composition comprising an aqueous solution of from about 5 to 30% w/v of an antibiotic compound selected from the group consisting of oxytetracycline and the pharmaceutically acceptable acid addition salts thereof, from about 0.8 to 1.1 molar proportions based on said antibiotic of a pharmaceutically acceptable magnesium compound soluble in said solution and from about 30 to 60% w/v of caprolactam or 2-piperidone, said composition having a pH of from about 7.5 to 9.5.

Further disclosed is a preferred doxycycline composition comprising an aqueous solution of from about 5 to 20% w/v of an antibiotic compound selected from the group consisting of doxycycline and the pharmaceutically acceptable acid addition salts thereof, from about 1.8 to 2.2 molar proportions based on said antibiotic of a pharmaceutically acceptable magnesium compound soluble in said solution, and from about 50 to 70% w/v of caprolactam or 2-piperidone, said composition having a pH value in the range of from about 3.5 to 7.5.

Additionally, there is disclosed a preferred chlortetracycline composition comprising an aqueous solution of from about 5 to 15% w/v of the antibiotic compound selected from the group consisting of chlortetracycline and the pharmaceutically acceptable acid addition salts thereof, from about 1.8 to 2.2 molar proportions based on said antibiotic of a pharmaceutically acceptable calcium compound soluble in said solution, and from about 60 to 70% w/v of caprolactam or 2-piperidone, said composition having a pH value in the range of from about 8.5 to 9.5.

DETAILED DESCRIPTION OF THE INVENTION

Caprolactam or 2-piperidone are present as cosolvents for the tetracycline antibiotics utilized in the compositions of this invention.

Caprolactam is also known as hexahydro-2H-azepin-2-one, $\epsilon$-caprolactam; 2-oxohexamethylenimine; 2-ketohexamethylenimine and aminocaproic lactam. It has an oral $LD_{50}$ of 1.66 gm/kg in rats and 590 mg/kg by intraperitoneal injection in mice.

2-Piperidone is also known as 5-aminopentanoic acid lactam and $\delta$-valerolactam. It has an oral $LD_{50}$ of 6.4 gm/kg in rats.

The use of the above solvents allows for minimum volume per dose and excellent syringeability due to the low viscosity of the resultant composition.

Oxytetracycline is a widely used tetracycline-type antibiotic. It is particularly described in U.S. Pat. No. 2,516,080. A preferred concentration range for oxytetracycline in the solutions of this invention is generally from about 5 to 30% w/v of the total in the form of the free base or a pharmaceutically acceptable acid addition salt. The preferred form is the free base with the particularly preferred concentration being from about 20 to 30% w/v.

Examples of suitable oxytetracycline acid addition salts which can be used include such pharmaceutically acceptable acid addition salts as the hydrochloride, hydrobromide and sulfate. However, the preferred acid addition salt is oxytetracycline hydrochloride.

Magnesium ions combine with oxytetracycline in solution to form magnesium-oxytetracycline chelates. Magnesium oxide is a convenient and preferred source of magnesium ions, but other magnesium compounds useful for this purpose include magnesium chloride, magnesium acetate, magnesium sulfate, magnesium ascorbate, magnesium lactate and magnesium gluconate. The preferred molar ratio of magnesium to oxytetracycline in these compositions is from about 0.8 to 1.1.

Caprolactam or 2-piperidone is present as a co-solvent for the oxytetracycline magnesium chelate, preferably in a concentration of from about 30 to 60% w/v, with the particularly preferred concentration being from about 40 to 50% w/v.

The pH value is preferably adjusted if necessary to pH 7.5 to 9.5. The particularly preferred range is pH 8.5 to 9.0. The pH can be adjusted with organic bases such as aminoethanol, dimethylaminoethanol, dimethylamine and so forth. Of these compounds, aminoethanol is the preferred compound.

Oxytetracycline is currently available for parenteral administration at a concentration of 50 mg./ml. Therefore a 500 Kg steer would require 200 ml. of a 50 mg./ml. product injected into 5 to 10 different areas in order to receive an effective dose. The compositions of this invention obviate this difficulty in that easily syringeable high dosage compositions are now possible, e.g., 200 mg./ml.

Doxycycline is a widely used tetracycline-type antibiotic of high potency and having a superior half-life. It is particularly described in U.S. Pat. No. 3,200,149 under the chemical name α-6-deoxy-5-oxytetracycline. A preferred concentration range for doxycycline in the solution of this invention is generally from about 1 to 25% by weight of the total in the form of the free base or a pharmaceutically acceptable acid addition salt. The preferred form is the free base with the particularly preferred concentration being from about 5% to 20% w/v, especially from about 10% to 20% w/v.

Examples of suitable doxycycline acid addition salts which can be used include such pharmaceutically acceptable acid addition salts as hydrochloride, hydrobromide and sulfate. However, the preferred acid addition salt is doxycycline hydrochloride, e.g., in the form of doxycycline hyclate, which is doxycycline hydrochloride hemiethanolate hemihydrate.

Magnesium ions combine with doxycycline in solution to form magnesium-doxycycline chelates. Magnesium oxide is a convenient and preferred source of magnesium ions, but other magnesium compounds useful for the purpose of this invention include magnesium chloride, magnesium acetate and magnesium sulfate. The molar ratio of magnesium to doxycycline in these compositions is preferably about from 1.8 to 2.2.

Caprolactam or 2-piperidone is present as a co-solvent for the doxycycline, preferably in a concentration of from about 50 to 70% w/v. The pH value is preferably adjusted if necessary to pH 3.5 to 7.5. The pH can be adjusted by means of an acid that is pharmaceutically acceptable, such as hydrochloric acid or by means of an organic base, such as monoethanolamine.

Chlortetracycline is a widely used tetracycline-type antiobiotic. It is particularly described in U.S. Pat. No. 2,482,055. A preferred concentration range for chlortetracycline in the solutions of this invention is generally from about 5 to 15% w/v of the total in the form of the free base or a pharmaceutically acceptable acid addition salt. The preferred form is the acid addition salt with the particularly preferred concentration being from about 10 to 15% w/v.

Examples of suitable chlortetracycline acid addition salts which can be used include such pharmaceutically acceptable acid addition salts as hydrochloride, hydrobromide and sulfate. However, the preferred acid addition salt is chlortetracycline hydrochloride.

Calcium ions combine with chlortetracycline in solution to form calcium-tetracycline chelates. Calcium chloride is a convenient and preferred source of calcium ions, but other compounds useful for the purpose of this invention include calcium oxide, calcium acetate and calcium sulfate. The molar ratio of calcium to chlortetracycline in these compositions is preferably from about 1.8 to 2.2.

Caprolactam or 2-piperidone is present as a co-solvent, preferably in a concentration of from about 60 to 70% w/v. The pH value is preferably adjusted if necessary to pH 8.5 to 9.5. The particularly preferred range is pH 8.5 to 9.0. The pH can be adjusted with an organic base such as monoethanolamine or with a pharmaceutically acceptable acid, such as hydrochloric acid.

The tetracycline antibiotic compositions of this invention are easy to syringe over a wide temperature range and are characterized by good physical and chemical stability.

The use of these high potency tetracycline antibiotic compositions enables a reduction of the number of injections that must be administered to large animals, such as steers, in order to receive an effective dose.

The primary application of these compositions is as a parenteral composition but the new compositions can also be used for topical or oral application.

As an optional ingredient polyvinylpyrrolidone having a molecular weight of between about 5,000 and 100,000 (K-12 to 30) may also be present in these compositions in a concentration of from about 1 to 7% by weight. The polyvinylpyrrolidone preferred for this invention is one having an average molecular weight of about 10,000–17,000 (where K-value = 17). It is present in part as a co-solubilizer and may improve tissue toleration.

As optional cosolvents ingredients such as propylene glycol, polyethylene glycols and glycerol formal may be present at concentrations of up to 25% w/v.

The stability of these solutions for therapeutic administration is still further enhanced by the use of antioxidants such as sodium or magnesium formaldehyde sulfoxylate and monothioglycerol at levels of from about 0.01 to 1.0% by weight.

The compositions of this invention are preferably prepared by mixing the caprolactam or 2-piperidone with water at 50° C. and adding the antioxidant. The magnesium or calcium compound is then added and the antibiotic is added slowly with stirring until a clear solution results. The pH is then adjusted to the desired range. If polyvinylpyrrolidone or optional cosolvents are to be included, they are added to the water at the time of mixing the caprolactam or 2-piperidone.

EXAMPLE 1

|  | gm/100 ml |
|---|---|
| Oxytetracycline (based on a potency of 927 mcg/mg plus a | 5.81 |

-continued

|  | gm/100 ml |
|---|---|
| 5% overage) | |
| Magnesium Oxide | 0.46 |
| Caprolactam | 30.00 |
| Sodium formaldehyde sulfoxylate | 1.00 |
| 2-Aminoethanol | 0.08 |
| Water q.s. to | 100 ml |

The caprolactam was dissolved in water. The solution was warmed to about 50° C., and the sodium formaldehyde sulfoxylate was added and dissolved with stirring. The magnesium oxide was then slurried with the solution. The oxytetracycline was slowly added with stirring until a clear solution resulted. The solution was allowed to cool to room temperature and the pH adjusted to 8.5 with 2-aminoethanol. The solution was then brought up to volume with water.

The above solution containing 50 mg./ml. of oxytetracycline activity had a viscosity of 4.8 cts. at 25° C.

EXAMPLE 2

The following solution containing 200 mg/ml of oxytetracycline activity was prepared using the procedure described in Example 1.

|  | gm/100 ml |
|---|---|
| Oxytetracycline (based on a potency of 927 mcg/mg plus a 5% overage) | 22.65 |
| Magnesium Oxide | 1.85 |
| Caprolactam | 40.00 |
| Sodium formaldehyde sulfoxylate | 1.00 |
| 2-Aminoethanol | 0.30 |
| Water q.s. to | 100 ml |

The viscosity was 18 cts. at 25° C.

A comparable solution was prepared using 60 gm. of caprolactam instead of 40 gm. This solution had a viscosity of 45 cts. at 25° C.

EXAMPLE 3

The following solution containing 300 mg/ml of oxytetracycline activity was prepared using the procedure described in Example 1.

|  | gm/100 ml |
|---|---|
| Oxytetracycline (based on a potency of 927 mcg/mg plus a 5% overage) | 33.98 |
| Magnesium oxide | 2.77 |
| Caprolactam | 50.00 |
| Sodium formaldehyde sulfoxylate | 0.45 |
| Water q.s. to | 100 ml |

EXAMPLE 4

|  | gm/100 ml |
|---|---|
| Oxytetracycline (based on a potency of 927 mcg/mg plus a 5% overage) | 11.3 |
| Magnesium oxide | 0.92 |
| Caprolactam | 40.00 |
| Polyvinylpyrrolidone, K-17 | 5.00 |
| Sodiium formaldehyde sulfoxylate | 1.00 |
| 2-Aminoethanol | 0.08 |
| Water q.s. to | 100 ml |

The caprolactam and polyvinylpyrrolidone were dissolved in water. The procedure as described in Example 1 was then followed.

The resulting product containing 100 mg/ml of oxytetracycline activity had a viscosity of 27 cts at 25° C.

The substitution of 1.0 gm of monothioglycerol for the sodium formaldehyde sulfoxylate produced a similar product.

EXAMPLE 5

The following solution containing 200 mg/ml of oxytetracycline activity was prepared using the procedure described in Example 4.

|  | gm/100 ml |
|---|---|
| Oxytetracycline (based on a potency of 927 mcg/mg plus a 5% overage) | 22.65 |
| Magnesium oxide | 1.85 |
| Caprolactam | 40.00 |
| Polyvinylpyrrolidone, K-17 | 5.00 |
| Sodium formaldehyde sulfoxylate | 1.00 |
| 2-Aminoethanol | 0.08 |
| Water q.s. to | 100 ml. |

The viscosity was 38 cts at 25° C.

EXAMPLE 6

|  | gm/100 ml |
|---|---|
| Oxytetracycline hydrochloride (based on a potency of 925 mcg/mg plus a 5% overage) | 22.70 |
| Magnesium oxide | 1.85 |
| Caprolactam | 50.00 |
| Sodium formaldehyde sulfoxylate | 1.00 |
| 2-Aminoethanol | 6.72 |
| Water q.s. to | 100 ml |

The caprolactam was dissolved in water. The solution was warmed to about 50° C. and the sodium formaldehyde sulfoxylate was added and dissolved with stirring. The magnesium oxide was then slurried with the solution. The oxytetracycline hydrochloride was slowly added with stirring. The pH then raised with addition of the monoethanolamine until solution resulted and the pH was finally adjusted to 8.5. The solution was then brought up to volume with water.

The above solution containing 200 mg/ml of oxytetracycline had a viscosity of 37 cts. at 25° C.

EXAMPLE 7

|  | gm/100 ml |
|---|---|
| Oxytetracycline hydrochloride (based on a potency of 925 mcg/mg plus a 5% overage) | 22.70 |
| Magnesium oxide | 1.85 |
| Caprolactam | 40.00 |
| Polyvinylpyrrolidone, K-17 | 5.00 |
| Monothioglycerol | 1.00 |
| 2-Aminoethanol | 7.87 |
| Water q.s. to | 100 ml |

The caprolactam and polyvinylpyrrolidone were dissolved in water. The procedure as described in Example 6 was then followed.

The resulting product containing 200 mg/ml of oxytetracycline activity, had a viscosity of 56 cts. wt. 25° C.

EXAMPLE 8

|  | gm/100 ml |
|---|---|
| Oxytetracycline (based on a potency of 927 mcg/mg plus a 5% overage) | 5.81 |

| | gm/100 ml |
|---|---|
| Magnesium oxide | 0.46 |
| 2-Piperidone | 30.00 |
| Sodium formaldehyde sulfoxylate | 1.00 |
| 2-Aminoethanol | 0.08 |
| Water q.s. to | 100 ml |

The 2-piperidone was dissolved in water. The solution was warmed to about 50° C. and the sodium formaldehyde sulfoxylate was added and dissolved with stirring. The magnesium oxide was then slurried with the solution. The oxytetracycline was slowly added with stirring until a clear solution resulted. The solution was allowed to cool to room temperature and the pH adjusted to 8.5 with 2-aminoethanol. The solution was then brought up to volume with water.

The above solution containing 50 mg/ml of oxytetracycline activity had a viscosity of 4.1 cts. at 25° C.

EXAMPLE 9

The following solution containing 200 mg/ml of oxytetracycline activity was prepared using the procedure described in Example 8.

| | gm/100 ml |
|---|---|
| Oxytetracycline (based on a potency of 927 mcg/mg plus a 5% overage) | 22.65 |
| Magnesium oxide | 1.85 |
| 2-Piperidone | 40.00 |
| Sodium formaldehyde sulfoxylate | 1.00 |
| 2-Aminoethanol | 0.30 |
| Water q.s. to | 100 ml |

The viscosity was 15 cts at 25° C.

The substitution of 1.0 gm of monothioglycerol for the sodium formaldehyde sulfoxylate produced a product similar to the above.

EXAMPLE 10

The following solution containing 300 mg/ml of oxytetracycline activity was prepared using the procedure described in Example 8.

| | gm/100 ml |
|---|---|
| Oxytetracycline (based on a potency of 927 mcg/mg plus a 5% overage) | 33.98 |
| Magnesium oxide | 2.77 |
| 2-Piperidone | 50.00 |
| Sodium formaldehyde sulfoxylate | 1.00 |
| 2-Aminoethanol | 0.45 |
| Water q.s. to | 100 ml |

The viscosity was 96 cts at 25° C.

EXAMPLE 11

The following solution containing 200 mg/ml of oxytetracycline activity was prepared using the procedure described in Example 8.

| | gm/100 ml |
|---|---|
| Oxytetracycline (based on a potency of 927 mcg/mg plus a 5% overage) | 22.65 |
| Magnesium oxide | 1.85 |
| 2-Piperidone 50.00 | |
| Sodium formaldehyde sulfoxylate | 1.00 |
| 2-Aminoethanol | 0.45 |
| Water q.s. to | 100 ml |

The viscosity was 39 cts. at 25° C.

The substitution of 0.44 gm of magnesium formaldehyde sulfoxylate produced a similar product.

EXAMPLE 12

| | gm/100 ml |
|---|---|
| Oxytetracycline (based on a potency of 927 mcg/mg plus a 5% overage) | 11.3 |
| Magnesium oxide | 0.92 |
| 2-Piperidone | 40.00 |
| Polyvinylpyrrolidone, K-17 | 5.00 |
| Sodium formaldehyde sulfoxylate | 1.00 |
| 2-Aminoethanol | 0.08 |
| Water q.s. to | 100 ml |

The 2-piperidone and polyvinylpyrrolidone were dissolved in water. The procedure as described in Example 8 was then followed.

The resulting product containing 100 mg/ml of oxytetracycline activity had a viscosity of 22 cts at 25° C.

EXAMPLE 13

The following solution containing 200 mg/ml of oxytetracycline activity was prepared using the procedure described in Example 12.

| | gm/100 ml |
|---|---|
| Oxytetracycline (based on a potency of 927 mcg/mg plus a 5% overage) | 22.65 |
| Magnesium oxide | 1.85 |
| 2-Piperidone 40.00 | |
| Polyvinylpyrrolidone, K-17 | 5.00 |
| Sodium formaldehyde sulfoxylate | 1.00 |
| 2-Aminoethanol | 0.30 |
| Water q.s. to | 100 ml |

The viscosity was 31 cts at 25° C.

The substitution of 1.0 gm. of monothioglycerol for the sodium formaldehyde sulfoxylate produced a similar product.

EXAMPLE 14

| | gm/100 ml |
|---|---|
| Oxytetracycline hydrochloride (based on a potency of 925 mcg/mg plus a 5% overage) | 22.70 |
| Magnesium oxide | 1.85 |
| 2-Piperidone | 50.00 |
| Sodium formaldehyde sulfoxylate | 1.00 |
| 2-Aminoethanol | 7.68 |
| Water q.s. to | 100 ml |

The 2-piperidone was dissolved in water. The solution was warmed to about 50° C. and the sodium formaldehyde sulfoxylate was added and dissolved with stirring. The magnesium oxide was then slurried with the solution. The oxytetracycline hydrochloride was slowly added with stirring. The pH was then raised with addition of the monoethanolamine until solution resulted and the pH was finally adjusted to 8.5. The solution was then brought up to volume with water.

The above solution containing 200 mg/ml of oxytetracycline activity had a viscosity of 32 cts. at 25° C.

EXAMPLE 15

| | gm/100 ml |
|---|---|
| Oxytetracycline hydrochloride (based on a potency of 925 mcg/mg plus a 5% overage) | 22.70 |
| Magnesium oxide | 1.85 |
| 2-Piperidone | 40.00 |
| Polyvinylpyrrolidone, K-17 | 5.00 |
| Sodium formaldehyde sulfoxylate | 1.00 |
| 2-Aminoethanol | 6.72 |
| Water q.s. to | 100 ml |

The 2-piperidone and polyvinylpyrrolidone were dissolved in water. The procedure as described in Example 14 was then followed.

The resulting product containing 200 mg/ml of oxytetracycline activity had a viscosity of 49 cts at 25° C.

EXAMPLE 16

| | gm/100 ml |
|---|---|
| Doxycycline (based on a potency of 960 mcg/mg plus a 5% overage) | 5.47 |
| Magnesium oxide | 1.00 |
| Caprolactam | 60.00 |
| Monothioglycerol | 1.00 |
| Concentrated hydrochloric acid | 1.90 |
| Water q.s. to | 100 ml |

The caprolactam was dissolved in water. The solution was warmed to about 50° C. and the monothioglycerol was added and dissolved with stirring. The magnesium oxide was added and slurried with the solution. The doxycycline was added with stirring. The pH was then lowered with addition of the concentrated hydrochloric acid until solution resulted and the pH was finally adjusted to 5.2. The solution was then brought up to volume with water.

The above solution containing 50 mg/ml of doxycycline activity had a viscosity of 17 cts at 25° C.

A comparable solution was also made by adjusting the pH to 7.2.

EXAMPLE 17

The following solution containing 100 mg/ml of doxycycline acticity was prepared using the procedure described in Example 16.

| | gm/100 ml |
|---|---|
| Doxycycline (based on a potency of 960 mcg/mg plus a 5% overage) | 10.93 |
| Magnesium oxide | 1.99 |
| Caprolactam | 40.00 |
| Monothioglycerol | 1.00 |
| Concentrated hydrochloric acid | 3.80 |
| Water q.s. to | 100 ml |

EXAMPLE 18

The following solution containing 200 mg/ml of doxycycline activity was prepared using the procedure described in Example 16.

| | gm/100 ml |
|---|---|
| Doxycycline (based on a potency of 960 mcg/mg plus a 5% overage) | 21.85 |
| Magnesium oxide | 3.99 |
| Caprolactam | 60.00 |
| Monothioglycerol | 1.00 |
| Concentrated hydrochloric acid | 7.30 |
| Water q.s. to | 100 ml |

The substitution of 0.30 gm of sodium formaldehyde sulfoxylate or magnesium formaldehyde sulfoxylate for the monothioglycerol produced products similar to the above.

EXAMPLE 19

| | gm/100 ml |
|---|---|
| Doxycycline (based on a potency of 960 mcg/mg plus a 5% overage) | 10.93 |
| Magnesium oxide | 0.67 |
| Magnesium chloride hexahydrate | 6.30 |
| Caprolactam | 60.00 |
| Polyvinylpyrrolidone, K-17 | 5.00 |
| Monothioglycerol | 10.00 |
| Concentrated hydrochloric acid | 1.00 |
| Water q.s. to | 100 ml |

The caprolactam and the polyvinylpyrrolidone were dissolved in water. The solution was warmed to about 50° C. and the monothioglycerol was added and dissolved. The magnesium chloride and magnesium oxide was added with stirring. The doxycycline was slowly added with stirring until solution resulted. The solution was allowed to cool to room temperature and the pH adjusted to 5.2 with concentrated hydrochloric acid. The solution was then brought up to volume with water.

The above solution containing 100 mg/ml of doxycycline activity had a viscosity of 94 cts at 25° C.

EXAMPLE 20

The following solution containing 200 mg/ml of doxycycline activity was prepared using the procedure of Example 19.

| | gm/100 ml |
|---|---|
| Doxycycline (based on a potency of 960 mcg/ml plus a 5% overage) | 21.85 |
| Magnesium oxide | 1.21 |
| Magnesium chloride hexahydrate | 16.17 |
| Caprolactam | 60.00 |
| Polyvinylpyrrolidone, K-17 | 5.00 |
| Monothioglycerol | 10.00 |
| Concentrated hydrochloric acid | 0.30 |
| Water q.s. to | 100 ml |

The viscosity was 1,500 cts at 25° C.

EXAMPLE 21

| | gm/100 ml |
|---|---|
| Doxycycline (based on a potency of 960 mcg/mg plus a 5% overage) | 10.93 |
| Magnesium oxide | 0.36 |
| Magnesium chloride hexahydrate | 7.87 |
| Caprolactam | 50.00 |
| Propylene Glycol | 25.00 |
| Monothioglycerol | 10.00 |
| Monoethanolamine | 0.90 |
| Water q.s. to | 100 ml |

The caprolactam and propylene glycol were added to water and stirred. The procedure as described in Example 16 was then followed except that the pH was adjusted with monoethanolamine.

The above solution containing 100 mg/ml of doxycycline activity had a viscosity of 56 cts at 25° C.

EXAMPLE 22

The following solution containing 100 mg/ml of doxycycline activity was prepared using the procedure described in Example 19.

|  | gm/100 ml |
|---|---|
| Doxycycline hyclate (based on a potency of 850 mcg/mg plus a 5% overage) | 12.35 |
| Magnesium oxide | 1.99 |
| Caprolactam | 60.00 |
| Polyvinylpyrrolidone, K-17 | 5.00 |
| Concentrated hydrochloric acid | 2.50 |
| Water q.s. to | 100 ml |

The viscosity was 55 cts at 25° C.

EXAMPLE 23

The following solution containing 100 mg/ml of doxycycline activity was prepared using the procedure described in Example 21.

|  | gm/100 ml |
|---|---|
| Doxycycline hyclate (based on a potency of 850 mcg/mg plus a 5% overage) | 12.35 |
| Magnesium oxide | 0.39 |
| Magnesium chloride hexahydrate | 7.87 |
| Caprolactam | 50.00 |
| Propyleneglycol | 25.00 |
| Monoethanolamine | 1.60 |
| Water q.s. to | 100 ml |

The viscosity was 61 cts at 25° C.

EXAMPLE 24

|  | gm/100 ml |
|---|---|
| Doxycycline (based on a potency of 960 mcg/mg plus a 5% overage) | 5.47 |
| Magnesium oxide | 1.00 |
| 2-Piperidone | 60.00 |
| Monothioglycerol | 1.00 |
| Concentrated hydrochloric acid | 1.90 |
| Water q.s. to | 100 ml |

The 2-piperidone was dissolved in water. The solution was warmed to about 50° C. and the monothioglycerol was added and dissolved with stirring. The magnesium oxide was added and slurried with the solution. The doxycycline was added with stirring. The pH was then lowered with addition of the concentrated hydrochloric acid until solution resulted and the pH was finally adjusted to 5.2. The solution was then brought up to volume with water.

The above solution containing 50 mg/ml of doxycycline activity had a viscosity of 9.5 cts at 25° C.

A solution comparable to the above was also made by adjusting the pH to 7.2.

EXAMPLE 25

The following solution containing 100 mg/ml of doxycycline activity was prepared using the procedure described in Example 24.

|  | gm/100 ml |
|---|---|
| Doxycycline (based on a potency of 960 mcg/mg plus a 5% overage) | 10.93 |
| Magnesium oxide | 1.99 |
| 2-Piperidone | 40.00 |
| Monothioglycerol | 1.00 |
| Concentrated hydrochloric acid | 3.80 |
| Water q.s. to | 100 ml |

The viscosity was 8.5 cts at 25° C.

Solutions comparable to the above were also made by adjusting the pH to 4.2 and 3.5, respectively.

EXAMPLE 26

The following solution containing 200 mg/ml of doxycycline activity was prepared using the procedure described in Example 24.

|  | gm/100 ml |
|---|---|
| Doxycycline (based on a potency of 960 mcg/mg plus a 5% overage) | 21.85 |
| Magnesium oxide | 3.99 |
| 2-Piperidone | 60.00 |
| Monothioglycerol | 1.00 |
| Concentrated hydrochloric acid | 7.30 |
| Water q.s. to | 100 ml |

The viscosity was 29 cts at 25° C.

EXAMPLE 27

|  | gm/100 ml |
|---|---|
| Doxycycline (based on a potency of 960 mcg/mg plus a 5% overage) | 10.93 |
| Magnesium oxide | 0.67 |
| Magnesium chloride hexahydrate | 6.30 |
| 2-Piperidone | 60.00 |
| Polyvinylpyrrolidone, K-17 | 5.00 |
| Monothioglycerol | 1.00 |
| Concentrated hydrochloric acid | 1.00 |
| Water q.s. to | 100 ml |

The 2-piperidone and the polyvinylpyrrolidone were dissolved in water. The solution was warmed to about 50° C. and the monothioglycerol added and dissolved. The magnesium chloride and magnesium oxide was added with stirring. The doxycycline was slowly added with stirring until solution resulted. The solution was allowed to cool to room temperature and the pH adjusted to 5.2 with hydrochloric acid. The solution was then brought up to volume with water.

The above solution containing 100 mg/ml of doxycycline activity had a viscosity of 72 cts at 25° C.

EXAMPLE 28

The following solution containing 200 mg/ml of doxycycline activity was prepared using the procedure described in Example 27.

|  | gm/100 ml |
|---|---|
| Doxycycline (based on a potency of 960 mcg/mg plus a 5% overage) | 21.85 |
| Magnesium oxide | 1.21 |
| Magnesium chloride hexahydrate | 16.17 |
| 2-Piperidone | 60.00 |
| Polyvinylpyrrolidone, K-17 | 5.00 |
| Monothioglycerol | 1.00 |
| Water q.s. to | 100 ml |

The viscosity was 780 cts at 25° C.

EXAMPLE 29

|  | gm/100 ml |
|---|---|
| Doxycycline (based on a potency of 960 mcg/mg plus a 5% overage) | 10.93 |
| Magnesium oxide | 0.36 |
| Magnesium chloride hexahydrate | 7.87 |
| 2-Piperidone | 50.00 |
| Propylene Glycol | 25.00 |
| Monothioglycerol | 1.00 |
| Monoethanolamine | .90 |
| Water q.s. to | 100 ml |

The 2-piperidone and propylene glycol were dissolved in water. The procedure as described in Example 27 was then followed, except that the pH was adjusted with monoethanolamine.

The above solution containing 100 mg/ml of doxycycline activity had a viscosity of 25 cts at 25° C.

EXAMPLE 30

The following solution containing 100 mg/ml of doxycycline activity was prepared using the procedure described in Example 27.

|  | gm/100 ml |
|---|---|
| Doxycycline hyclate (based on a potency of 850 mcg/mg plus a 5% overage) | 12.35 |
| Magnesium oxide | 1.99 |
| 2-Piperidone | 60.00 |
| Polyvinylpyrrolidone, K-17 | 5.00 |
| Concentrated hydrochloric acid | 2.50 |
| Water q.s. to | 100 ml |

The viscosity was 27 cts at 25° C.

EXAMPLE 31

The following solution containing 100 mg/ml of doxycycline activity was prepared using the procedures described in Example 29.

|  | gm/100 ml |
|---|---|
| Doxycycline hyclate (based on a potency of 850 mcg/mg plus a 5% overage | 12.35 |
| Magnesium oxide | 0.39 |
| Magnesium chloride hexahydrate | 7.87 |
| 2-Piperidone | 50.00 |
| Propylene glycol | 25.00 |
| Monoethanolamine | 1.60 |
| Water q.s. to | 100 ml |

The viscosity was 59 cts at 25° C.

EXAMPLE 32

|  | gm/100 ml |
|---|---|
| Chlortetracycline hydrochloride (based on a chlortetracycline hydrochloride potency of 950 mcg/mg plus a 5% overage) | 55.26 |
| Calcium chloride | 25.34 |
| Caprolactam | 60.00 |
| Monothioglycerol | 1.00 |
| 2-Aminoethanol | 1.84 |
| Water q.s. to | 100 ml |

Preparation

The caprolactam was dissolved in water. The solution was warmed to about 50° C. and the monothioglycerol was added and dissolved with stirring. The calcium chloride was then added and dissolved. The chlortetracycline hydrochloride was slowly added with stirring until a clear solution resulted. The solution was allowed to cool to room temperature and the pH adjusted to 9.0 with 2-aminoethanol. The solution was then brought up to volume with water.

The above solution containing 50 mg/ml of chlortetracycline hydrochloride activity had a viscosity of 13 cts at 25° C.

EXAMPLE 33

The following solution containing 100 mg/ml of chlortetracycline hydrochloride activity was prepared using the procedure described in Example 32.

|  | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| Caprolactam | 60.00 |
| Monothioglycerol | 1.00 |
| 2-Aminoethanol | 4.44 |
| Water q.s. to | 100 ml |

The viscosity was 47 cts at 25° C.

EXAMPLE 34

The following solution containing 150 mg/ml of chlortetracycline hydrochloride activity was prepared using the procedure described in Example 32.

|  | gm/100 ml |
|---|---|
| Chlortetracycline hydrochloride (based on a chlortetracycline hydrochloride potency of 950 mcg/mg plus a 5% overage) | 165.78 |
| Calcium chloride | 76.02 |
| Caprolactam | 60.00 |
| Monothioglycerol | 1.00 |
| 2-Aminoethanol | 5.28 |
| Water q.s. to | 100 ml |

The viscosity was 15 cts at 25° C.

EXAMPLE 35

The following solution containing 100 mg/ml of chlortetracycline hydrochloride activity was prepared using the procedure described in Example 32.

|  | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| Caprolactam | 70.00 |
| Monothioglycerol | 1.00 |
| 2-Aminoethanol | 4.44 |
| Water q.s. to | 100 ml |

The viscosity was 91 cts at 25° C.

EXAMPLE 36

|  | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| Caprolactam | 60.00 |

| | gm/100 ml |
|---|---|
| Polyvinylpyrrolidone, K-17 | 5.00 |
| Monothioglycerol | 1.00 |
| 2-Aminoethanol | 4.44 |
| Water q.s. to | 100 ml |

The caprolactam and polyvinylpyrrolidone were dissolved in water. The procedures described in Example 32 was then followed.

The above solution containing 100 mg/ml of chlortetracycline hydrochloride activity had a viscosity of 88 cts at 25° C.

EXAMPLE 37

| | gm/100 ml |
|---|---|
| Chlortetracycline hydrochloride (based on a chlortetracycline hydrochloride potency of 950 mcg/mg plus a 5% overage) | 55.26 |
| Calcium chloride | 25.34 |
| 2-Piperidone | 60.00 |
| Monothioglycerol | 1.00 |
| 2-Aminoethanol | 1.84 |
| Water q.s. to | 100 ml |

The 2-piperidone was dissolved in water. The solution was warmed to about 50° C. and the monothioglycerol was added and dissolved with stirring. The calcium chloride was then added and dissolved. The chlortetracycline hydrochloride was slowly added with stirring until a clear solution resulted. The solution was allowed to cool to room temperature and the pH adjusted to 9.0 with 2-aminoethanol. The solution was then brought up to volume with water.

The above solution containing 50 mg/ml of chlortetracycline hydrochloride had a viscosity of 10 cts at 25° C.

EXAMPLE 38

The following solution containing 100 mg/ml of chlortetracycline hydrochloride activity was prepared using the procedure described in Example 37.

| | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| 2-Piperidone | 60.00 |
| Monothioglycerol | 1.00 |
| 2-Aminoethanol | 4.44 |
| Water q.s. to | 100 ml |

The viscosity was 33 cts at 25° C.

EXAMPLE 39

The following solution containing 150 mg/ml of chlortetracycline hydrochloride activity was prepared using the procedure described in Example 37.

| | gm/100 ml |
|---|---|
| Chlortetracycline hydrochloride (based on a chlortetracycline hydrochloride potency of 950 mcg/mg plus a 5% overage) | 165.78 |
| Calcium chloride | 76.02 |
| 2-Piperidone | 60.00 |
| Monothioglycerol | 1.00 |
| 2-Aminoethanol | 5.28 |
| Water q.s. to | 100 ml |

The viscosity was 52 cts at 25° C.

EXAMPLE 40

The following solution containing 100 mg/ml of chlortetracycline hydrochloride activity was prepared using the procedure described in Example 37.

| | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| 2-Piperidone | 70.00 |
| Monothioglycerol | 1.00 |
| 2-Aminoethanol | 4.44 |
| Water q.s. to | 100 ml |

The viscosity was 47 cts at 25° C.

EXAMPLE 41

| | gm/100 ml |
|---|---|
| Chlortetracycline hydrochloride (based on a chlortetracycline hydrochloride potency of 950 mcg/mg plus a 5% overage) | 110.52 |
| Calcium chloride | 50.68 |
| 2-Piperidone | 60.00 |
| Polyvinylpyrrolidone, K-17 | 5.00 |
| Monothioglycerol | 1.00 |
| 2-Aminoethanol | 4.44 |
| Water q.s. to | 100 ml |

The 2-piperidone and polyvinylpyrrolidone were dissolved in water. The procedure described in Example 37 was then followed.

The above solution containing 100 mg/ml of chlortetracycline hydrochloride activity had a viscosity of 30 cts at 25° C.

The substitution of 0.20 gm of sodium formaldehyde sulfoxylate or magnesium formaldehyde sulfoxylate for the monothioglycerol produced similar products.

What is claimed is:

1. A liquid composition comprising an aqueous solution of a tetracycline antibiotic in caprolactam or 2-piperidone, said tetracycline being selected from the group consisting of oxytetracycline in a concentration of from about 5 to 30% w/v, doxycycline in a concentration of from about 5 to 20% w/v, chlortetracycline in a concentration of from about 5 to 15% w/v, and the pharmaceutically acceptable acid addition salts thereof, with the proviso that when said tetracycline antibiotic is oxytetracycline or its pharmaceutically-acceptable acid addition salts the caprolactam or 2-piperidone is present in a concentration of from about 30 to 60% w/v, when said tetracycline antibiotic is doxycycline or its pharmaceutically-acceptable acid addition salts the caprolactam or 2-piperidone is present in a concentration of from about 50 to 70% w/v, and when said tetracycline antibiotic is chlortetracycline or its pharmaceutically-acceptable acid addition salts the caprolactam or 2-piperidone is present in a concentration of from about 60 to 70% w/v.

2. A composition as claimed in claim 1 comprising an aqueous solution of from about 5 to 30% w/v of an antibiotic compound selected from the group consisting of oxytetracycline and the pharmaceutically acceptable acid addition salts thereof, from about 0.8 to 1.1 molar proportions based on said antibiotic of a pharmaceutically acceptable magnesium compound soluble in said solution and from about 30 to 60% w/v of caprolactam or 2-piperidone, said composition having a pH of from about 7.5 to 9.5.

3. A composition as claimed in claim 2 wherein said antibiotic compound is oxytetracycline.

4. A composition as claimed in claim 2 wherein said magnesium compound is introduced in the form of magnesium oxide.

5. A composition as claimed in claim 2 wherein said antibiotic compound is present at a level of from about 20 to 30% w/v.

6. A composition as claimed in claim 2 having a pH value of from about 8.5 to 9.

7. A composition as claimed in claim 2 wherein polyvinylpyrrolidone is also present in a concentration of from about 1 to 7% w/v.

8. A composition according to claim 1 comprising an aqueous solution of a tetracycline antibiotic in caprolactam.

9. An oxytetracycline composition comprising an aqueous solution of from about 20 to 30% w/v of oxytetracycline, from about 0.8 to 1.1 molar proportions of a pharmaceutically acceptable magnesium compound soluble in said solution, from about 40 to 50% w/v of caprolactam or 2-piperidone and from about 1 to 7% w/v of polyvinylpyrrolidone, said composition having a pH value in the range of from about 8.5 to 9.

10. A composition according to claim 9 comprising an aqueous solution of oxytetracycline in from about 40 to 50% w/v of caprolactam.

11. A composition as claimed in claim 1 comprising an aqueous solution of from about 5 to 20% w/v of an antibiotic compound selected from the group consisting of doxycycline and the pharmaceuticaly acceptable acid addition salts thereof, from about 1.8 to 2.2 molar proportions based on said antibiotic of a pharmaceutically acceptable magnesium compound soluble in said solution, and from about 50 to 70% w/v of caprolactam or 2-piperidone, said composition having a pH value in the range of from about 3.5 to 7.5.

12. A composition as claimed in claim 11 wherein said antibiotic is doxycycline.

13. A composition as claimed in claim 11 wherein said magnesium compound is introduced in the form of magnesium oxide.

14. A composition as claimed in claim 11 wherein said antibiotic compound is present at the level of from about 10 to 20% w/v.

15. A composition as claimed in claim 11 wherein polyvinylpyrrolidone is also present in a concentration of from about 1 to 7% w/v.

16. A doxycycline composition comprising an aqueous solution of from about 10 to 20% w/v of doxycycline, from about 1.8 to 2.2 molar proportions based on doxycycline of a pharmaceutically acceptable magnesium compound soluble in said solution, from about 50 to 70% w/v of caprolactam or 2-piperidone and from about 1 to 7% w/v of polyvinylpyrrolidone, said composition having a pH value in the range of from about 3.5 to 7.5.

17. A composition according to claim 16 comprising an aqueous solution of doxycycline in from about 50 to 70% w/v of caprolactam.

18. A composition as claimed in claim 1 comprising an aqueous solution of from about 5 to 15% w/v of an antibiotic compound selected from the group consisting of chlortetracycline and the pharmaceutically acceptable acid addition salts thereof, from about 1.8 to 2.2 molar proportions based on said antibiotic of a pharmaceutically acceptable calcium compound soluble in said solution, and from about 60 to 70% w/v of caprolactam or 2-piperidone, said composition having a pH value in the range of from about 8.5 to 9.5.

19. A composition as claimed in claim 18 wherein said antibiotic compound is chlortetracycline hydrochloride.

20. A composition as claimed in claim 18 wherein said calcium compound is introduced in the form of calcium chloride.

21. A composition as claimed in claim 18 wherein said antibiotic compound is present at a level of from about 10 to 15% w/v.

22. A composition as claimed in claim 18 wherein polyvinylpyrrolidone is also present in a concentration of from about 1 to w/v.

23. A chlortetracycline composition comprising an aqueous solution of from about 10 to 15% w/v of chlortetracycline, from about 1.8 to 2.2 molar proportions based on chlortetracycline of a pharmaceutically accpetable calcium compound soluble in said solution, from about 60 to 70% w/v of caprolactam or 2-piperidone, and from about 1 to 7% w/v of polyvinylpyrrolidone, said composition having a pH value in the range of from about 8.5 to 9.

24. A composition according to claim 23 comprising an aqueous solution of chlortetracycline in from about 60 to 70% w/v of caprolactam.

* * * * *